United States Patent
Tanaka

(10) Patent No.: US 10,856,830 B2
(45) Date of Patent: Dec. 8, 2020

(54) RADIATION IMAGING SYSTEM, RADIATION IMAGING APPARATUS, RADIATION IMAGING METHOD, AND STORAGE MEDIUM

(71) Applicant: CANON KABUSHIKI KAISHA, Tokyo (JP)

(72) Inventor: Hikaru Tanaka, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/135,255

(22) Filed: Sep. 19, 2018

(65) Prior Publication Data

US 2019/0015064 A1 Jan. 17, 2019

Related U.S. Application Data

(63) Continuation of application No. 15/475,386, filed on Mar. 31, 2017, now Pat. No. 10,111,640.

(30) Foreign Application Priority Data

Apr. 8, 2016 (JP) ................................. 2016-078431

(51) Int. Cl.
*G01J 1/42* (2006.01)
*A61B 6/00* (2006.01)

(52) U.S. Cl.
CPC ............ *A61B 6/54* (2013.01); *A61B 6/465* (2013.01); *A61B 6/56* (2013.01); *A61B 6/566* (2013.01)

(58) Field of Classification Search
CPC .. G01T 1/17; G01T 7/00; G01T 1/167; G01T 1/36; G01T 1/178
See application file for complete search history.

(56) References Cited

U.S. PATENT DOCUMENTS

| | | | |
|---|---|---|---|
| 9,413,995 B2 | 9/2016 | Ohguri | |
| 9,538,969 B2 | 1/2017 | Nishii et al. | |
| 10,111,640 B2 * | 10/2018 | Tanaka | ................ A61B 6/465 |
| 10,278,665 B2 | 5/2019 | Benndorf et al. | |
| 10,412,147 B2 | 9/2019 | Zheng | |
| 2006/0129669 A1 | 6/2006 | Kojima | |
| 2009/0129643 A1 | 5/2009 | Natanzon et al. | |
| 2014/0252205 A1 | 9/2014 | Tanaka | |
| 2014/0258907 A1 | 9/2014 | Tanaka | |

(Continued)

FOREIGN PATENT DOCUMENTS

| | | |
|---|---|---|
| JP | 2003-303056 | 10/2003 |
| JP | 2005-198801 | 7/2005 |
| JP | 2005-287937 | 10/2005 |

(Continued)

OTHER PUBLICATIONS

Kawamata, "Type Script Beginner Course which could be used for Large-Scale Development Projects and Small-Scale Development Projects" (2014).

*Primary Examiner* — David P Porta
*Assistant Examiner* — Mamadou Faye
(74) *Attorney, Agent, or Firm* — Venable LLP

(57) ABSTRACT

A radiation imaging system includes: an imaging unit configured to transfer a radiation image generated based on received radiation; and a control unit configured to determine, based on a transfer status of the radiation image, whether to continue or interrupt to transfer the radiation image.

18 Claims, 12 Drawing Sheets

(56) References Cited

U.S. PATENT DOCUMENTS

2015/0078527 A1    3/2015   Iwamoto et al.
2016/0213346 A1    7/2016   Benndorf et al.

FOREIGN PATENT DOCUMENTS

| JP | 2006-173681 | | 6/2006 |
|----|----|----|----|
| JP | 2006-344115 | | 12/2006 |
| JP | 2007-130877 | | 5/2007 |
| JP | 2013240433 | A | 12/2013 |
| JP | 2014-175726 | | 9/2014 |
| WO | 2015/006903 | | 1/2015 |
| WO | 2015/043948 | | 4/2015 |

* cited by examiner

FIG. 9A

| IMAGE SIZE [pixels×pixels] | REDUCED IMAGE DATA DISPLAY TIME [msec] | WHOLE IMAGE DATA DISPLAY TIME [msec] |
|---|---|---|
| 2800×3408 | 8000 | 33000 |
| 3320×3408 | 8930 | 38570 |
| 2192×2800 | 6220 | 22300 |

FIG. 9B

| RADIATION IMAGING UNIT | IMAGE SIZE [pixels×pixels] | FIRST TIME-OUT TIME a [msec] | SECOND TIME-OUT TIME b [msec] |
|---|---|---|---|
| IMAGING UNIT A | 2800×3408 | 8000 | 33000 |
| IMAGING UNIT B | 3320×3408 | 8930 | 38570 |
| IMAGING UNIT C | 3320×3408 | 8930 | 38570 |
| IMAGING UNIT D | 3320×3408 | 8930 | 38570 |
| IMAGING UNIT E | 2192×2800 | 6220 | 22300 |
| IMAGING UNIT F | 2192×2800 | 6220 | 22300 |

FIG. 12

| IMAGING CONDITION | RADIATION IMAGING UNIT | ACCUMULATION TIME [msec] | IMAGING PART | IMAGING DIRECTION |
|---|---|---|---|---|
| IMAGING CONDITION 1 | IMAGING UNIT A | 500 | CHEST | PA |
| IMAGING CONDITION 2 | IMAGING UNIT A | 200 | STOMACH | AP |
| IMAGING CONDITION 3 | IMAGING UNIT A | 3000 | BUTTOCK | RL |
| IMAGING CONDITION 4 | IMAGING UNIT B | 3000 | BUTTOCK | RL |
| IMAGING CONDITION 5 | IMAGING UNIT B | 600 | CHEST | PA |
| IMAGING CONDITION 6 | IMAGING UNIT C | 300 | KNEE | LL |
| IMAGING CONDITION 7 | IMAGING UNIT C | 100 | HAND | AP |
| IMAGING CONDITION 8 | IMAGING UNIT C | 150 | HAND | RL |
| ... | ... | ... | ... | ... |

RADIATION IMAGING SYSTEM, RADIATION IMAGING APPARATUS, RADIATION IMAGING METHOD, AND STORAGE MEDIUM

BACKGROUND OF THE INVENTION

Field of the Invention

The present invention relates to a radiation imaging system, a radiation imaging apparatus, a radiation imaging method, and a storage medium.

Description of the Related Art

The digitization of radiation images allows the user to confirm an image immediately after radiation imaging, thereby improving a workflow, as compared with conventional radiation imaging using a film. For example, a radiation imaging system in which an image is wirelessly communicated from a radiation imaging apparatus via a wireless communication medium, the portability of the radiation imaging apparatus is improved by wirelessly communicating an image. In addition, an imaging location is not limited to an imaging room and imaging can be performed in various locations.

When communicating an image, it may be impossible to stably communicate the image due to a change in communication environment caused by the influence of noise or the like which interferes communication. In an arrangement disclosed in Japanese Patent Laid-Open No. 2013-240433, in order to reliably perform communication, stable image communication is ensured by enabling image communication in a good communication environment and prohibiting communication in an environment other than the good environment.

In the arrangement disclosed in Japanese Patent Laid-Open No. 2013-240433, however, communication is prohibited in an environment other than the good environment. Thus, in the arrangement disclosed in Japanese Patent Laid-Open No. 2013-240433, it is impossible to perform image communication when a wireless environment is not relatively good, and the operation of an operator is restricted by an image communication operation until the communication environment is recovered to the good state.

The present invention has been made in consideration of the above problem, and provides a radiation imaging technique capable of controlling transfer by determining, based on the transfer status of a radiation image, whether to continue or interrupt transfer.

SUMMARY OF THE INVENTION

According to one aspect of the present invention, there is provided a radiation imaging system comprising: an imaging unit configured to transfer a radiation image generated based on received radiation; and a control unit configured to determine, based on a transfer status of the radiation image, whether to continue or interrupt to transfer the radiation image.

According to another aspect of the present invention, there is provided a radiation imaging system comprising: an imaging unit configured to transfer a radiation image generated based on received radiation; and a reception control unit configured to determine, based on a transfer status of the radiation image, whether to continue or end to receive the radiation image.

According to one aspect of the present invention, there is provided a radiation imaging method comprising: transferring a radiation image generated based on received radiation; and controlling to determine, based on a transfer status of the radiation image, whether to continue or interrupt to transfer the radiation image.

According to one aspect of the present invention, there is provided a radiation imaging method comprising: transferring a radiation image generated based on received radiation; and determining, based on a transfer status of the radiation image, whether to continue or end to transfer the radiation image.

According to the present invention, it is possible to provide a radiation imaging technique capable of controlling transfer by determining, based on the transfer status of a radiation image, whether to continue or interrupt transfer.

Further features of the present invention will become apparent from the following description of exemplary embodiments (with reference to the attached drawings).

BRIEF DESCRIPTION OF THE DRAWINGS

FIG. 9A is a table exemplifying the relationship between an image size and image data display times;

FIG. 9B is a table exemplifying a combination of a radiation imaging unit and time-out times according to the embodiment;

FIG. 12 is a table showing an example of a combination of an imaging condition and an accumulation time according to the third embodiment.

DESCRIPTION OF THE EMBODIMENTS

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments. In this specification, radiation may be, for example, electromagnetic waves, α-rays, β-rays, γ-rays, or the like. The arrangement of a radiation imaging system according to each embodiment will be described below with reference to the accompanying drawings.

First Embodiment

In the first embodiment, an arrangement will be described in which transfer is controlled on the radiation imaging unit (radiation imaging apparatus) side by determining, based on the transfer status of a radiation image, whether to continue or interrupt transfer. In a radiation imaging system according to this embodiment, after completion of transfer of reduced image data obtained by reducing a generated radiation image, a radiation imaging unit transfers the generated radiation image (whole image data). The transfer status is based on comparison between an elapsed time (measured time) taken to transfer the radiation image and a set interrupt determination time, and the radiation imaging system determines whether to continue or interrupt transfer. In the first embodiment, it is possible to control image communication so as to complete image communication by spending a long time and allow the operator to start the next activity early even if a wireless environment is not relatively good.

Figure 1:
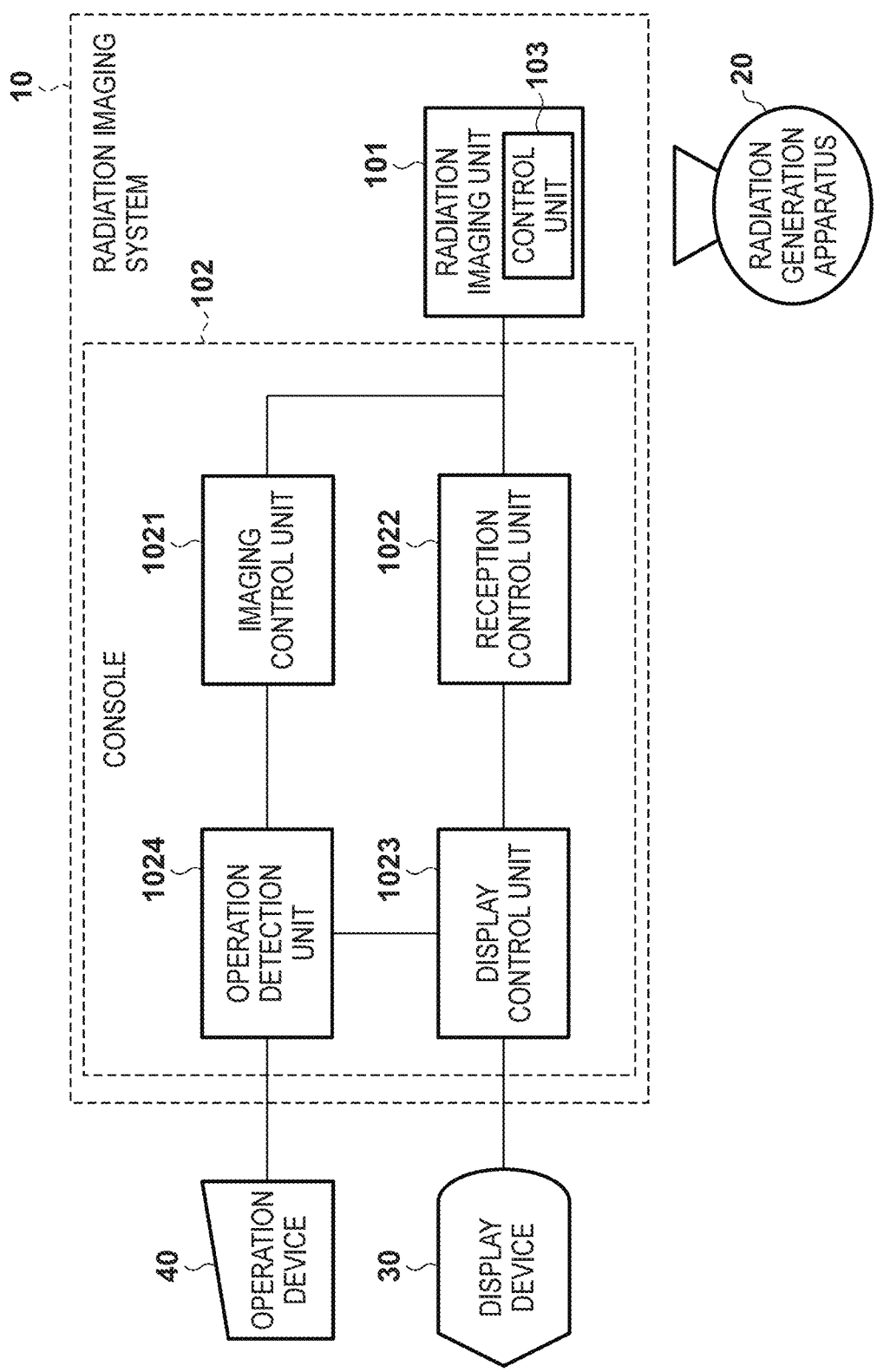
FIG. 1 is a view showing the arrangement of a radiation imaging system according to an embodiment.

FIG. 1 is a view showing an example of the arrangement of a radiation imaging system 10 according to the first embodiment. The radiation imaging system 10 includes, as its functional components, a plurality of radiation imaging units 101 and a console 102 (control apparatus). In the radiation imaging system 10, the radiation imaging unit (radiation imaging apparatus) 101 can transfer a radiation image generated based on received radiation. The radiation imaging unit 101 receives radiation from a radiation generation apparatus 20, generates a digital image based on the received radiation, and transfers the generated radiation image. The radiation imaging unit 101 includes a control unit 103 for controlling imaging and transfer of a radiation image. The control unit 103 can control transfer by determining, based on the transfer status of the radiation image, whether to continue or interrupt transfer. The console 102 (control apparatus) decides the radiation imaging unit 101 to be used among the plurality of radiation imaging units, and sends an imaging preparation request to the radiation imaging unit 101 or performs display of the digital image received from the radiation imaging unit 101 and an image editing operation.

The console 102 (control apparatus) includes, as its functional components, an imaging control unit 1021, a reception control unit 1022, a display control unit 1023, and an operation detection unit 1024.

In the console 102 (control apparatus), the imaging control unit 1021 can send an imaging preparation request to the radiation imaging unit 101, set time-out times in the radiation imaging unit 101, control imaging in the radiation imaging unit, and perform transfer control for transferring or retransferring captured image data. The reception control unit 1022 can perform the reception processing of the image (image data) transmitted from the radiation imaging unit 101, and determine, based on the transfer status of the radiation image, whether to continue or end the reception of the radiation image. The display control unit 1023 is connected to a display device 30, and performs display control for displaying, on the display device 30, the image received by the reception control unit 1022. The operation detection unit 1024 is connected to an operation device 40, and receives, from the operation device 40, information input by the operator. The operation detection unit 1024 is connected to the imaging control unit 1021 and the display control unit 1023, and the imaging control unit 1021 and the display control unit 1023 can operate based on the input information from the operation detection unit 1024.

Communication between the radiation imaging unit 101 and the console 102 (control apparatus) may be implemented by wired communication or wireless communication. In the case of wireless communication, either the radiation imaging unit 101 or the console 102 (control apparatus) functions as an access point.

(Processing Procedure of Console 102)

Figure 2:
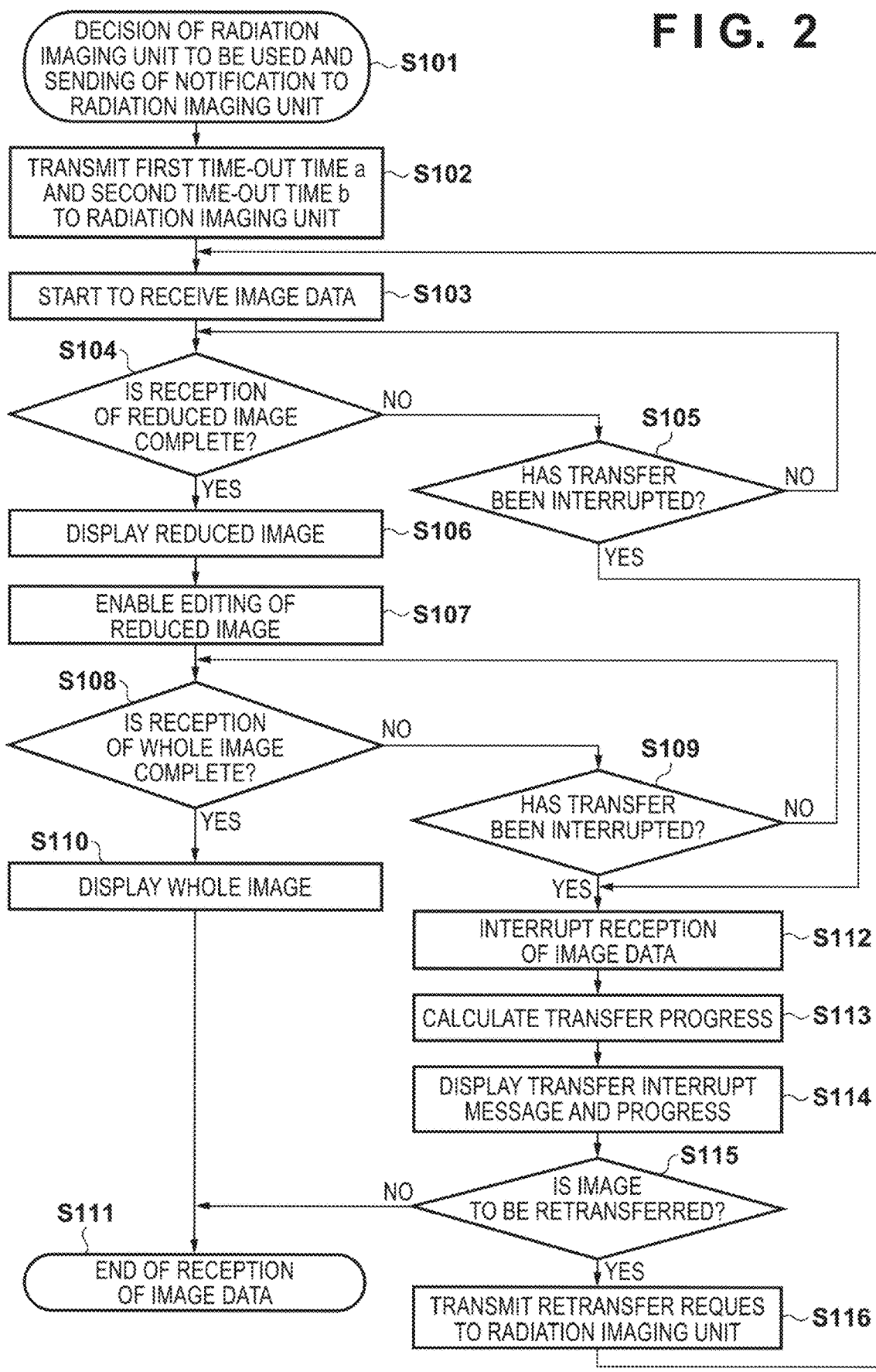
FIG. 2 is a flowchart illustrating the processing procedure of a console according to the embodiment.

The processing procedure of the console 102 of the radiation imaging system 10 will be described next. FIG. 2 is a flowchart illustrating the processing procedure of the console 102 from when the console 102 of the radiation imaging system 10 specifies the radiation imaging unit 101 to be used for imaging to perform radiation imaging until the radiation imaging ends.

Figure 5:
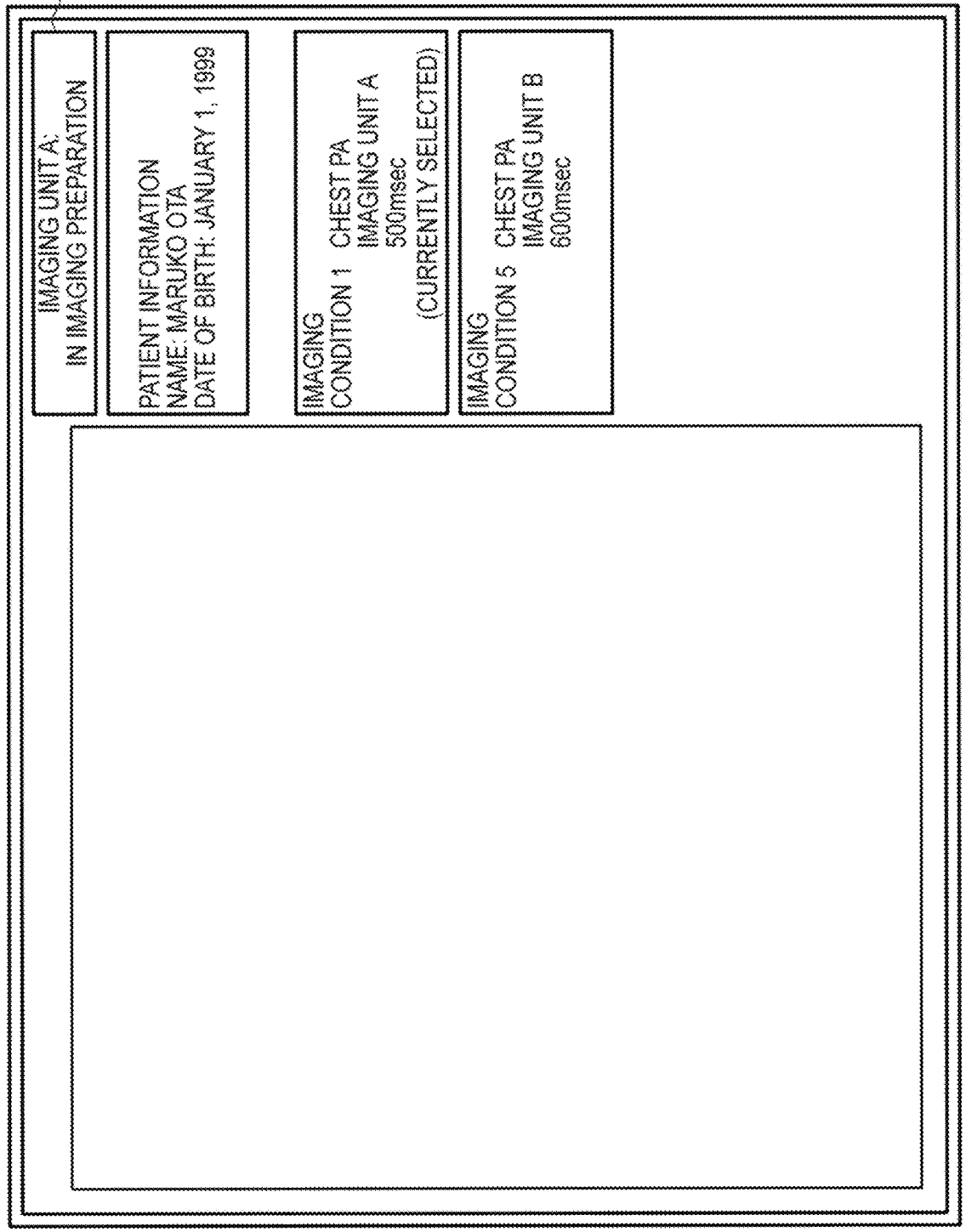
FIG. 5 is a view showing a display example of reduced image data on an external display device.

In step S101, the imaging control unit 1021 of the console 102 decides the radiation imaging unit 101 to be used for imaging among the plurality of radiation imaging units (to be also simply referred to as "imaging units" hereinafter), and sends a notification to the decided radiation imaging unit 101. FIG. 5 is a view showing a display example on the display device 30. For example, on a screen displayed on the display device 30 shown in FIG. 5, the state of the radiation imaging unit to be used for radiation imaging, patient information, and imaging conditions are displayed. A linked imaging unit is set in each imaging condition. In the display example of FIG. 5, for example, imaging unit A corresponds to imaging condition 1 (imaging part: CHESTPA, time: 500 msec), and imaging unit B corresponds to imaging condition 5 (imaging part: CHESTPA, time: 600 msec). Based on selection of the imaging condition input via a GUI, an external operation device, or the like, the console 102 can decide the radiation imaging unit 101 to be used for radiation imaging. In the display example of FIG. 5, imaging condition 1 is in a selected state (currently selected), and "in imaging preparation" is currently displayed on state display 501 of the imaging unit (in this case, imaging unit A) to be used for imaging under imaging condition 1.

In step S102, the imaging control unit 1021 sets interrupt determination times based on the image size of the radiation imaging unit 101. The interrupt determination times include the first interrupt determination time for determining the interrupt of transfer of the reduced image data, and the second interrupt determination time for determining the interrupt of transfer of the generated radiation image data (whole image data). The second interrupt determination time is a time longer than the first interrupt determination time. The imaging control unit 1021 transmits, to the radiation imaging unit 101, the first interrupt determination time (first time-out time a) and second interrupt determination time (second time-out time b) corresponding to the radiation imaging unit 101 decided in step S101. In this example, the first interrupt determination time (first time-out time a) corresponds to a time (reduced image data display time) taken to display, on the display device 30, the reduced image data obtained by reducing the image generated by the imaging unit, and the second interrupt determination time (second time-out time b) corresponds to a time (whole image data display time) taken to display, on the display device 30, the radiation image (whole image data) generated by the imaging unit.

FIG. 9A is a table exemplifying the relationship between the image size and the image data display time. FIG. 9B is a table exemplifying a combination of the radiation imaging unit and the time-out times according to the embodiment. FIG. 9B exemplifies a combination of the image size set in each radiation imaging unit, the first time-out time a, and the second time-out time b. The imaging control unit 1021 includes a nonvolatile storage unit for storing the tables shown in FIGS. 9A and 9B, and obtains the first interrupt determination time (first time-out time a) and second interrupt determination time (second time-out time b) corresponding to the radiation imaging unit 101 decided in step S101 from the table shown in FIG. 9B, and transmits them to the radiation imaging unit 101. Since imaging unit A has been selected in step S101, the imaging control unit 1021 transmits, to the radiation imaging unit 101, "8000 msec" as the first interrupt determination time (first time-out time a) corresponding to imaging unit A and "33000 msec" as the second interrupt determination time (second time-out time b).

Note that the imaging control unit 1021 may decide the first time-out time a and the second time-out time b from the image data display times complying with the image size of the imaging unit. For example, the image size of imaging unit A is 2800 (pixels)×3408 (pixels), and the imaging control unit 1021 can obtain, from the table shown in FIG. 9A, the image data display times (reduced image data display time: 8000 msec, whole image data display time: 33000 msec) corresponding to this image size, and transmit them as the first interrupt determination time (first time-out time a) and the second interrupt determination time (second time-out time b) to the radiation imaging unit 101.

In step S103, the reception control unit 1022 receives the transferred image. The reception control unit 1022 starts to receive the image data by using, as a trigger, the start of transmission of the image data by the radiation imaging unit 101.

In step S104, the reception control unit 1022 determines whether the reception of the reduced image data is complete. If the reception of the reduced image data is complete (YES in step S104), the process advances to step S106; otherwise (NO in step S104), the process advances to step S105. The reception control unit 1022 determines whether the reception of the reduced image data is complete, and determines in step S105 whether the radiation imaging unit 101 has interrupted the image transfer. When the radiation imaging unit 101 interrupts the image transfer, it notifies the console 102 of the interrupt of the image transfer. Based on the notification transmitted from the radiation imaging unit 101, the reception control unit 1022 can determine whether the radiation imaging unit 101 has interrupted the image transfer. If the radiation imaging unit 101 has interrupted the image transfer (YES in step S105), the process advances to step S112.

On the other hand, if the radiation imaging unit 101 has not interrupted the image transfer (NO in step S105), the process returns to step S104, and the same processing is executed in step S104. In step S104, if it is determined that the reception of the reduced image data is complete (YES in step S104), the process advances to step S106. The reception control unit 1022 determines whether the reception of the reduced image data is complete. If the reception of the reduced image data is complete, the display control unit 1023 displays the reduced image data on the display device 30.

Figure 6:
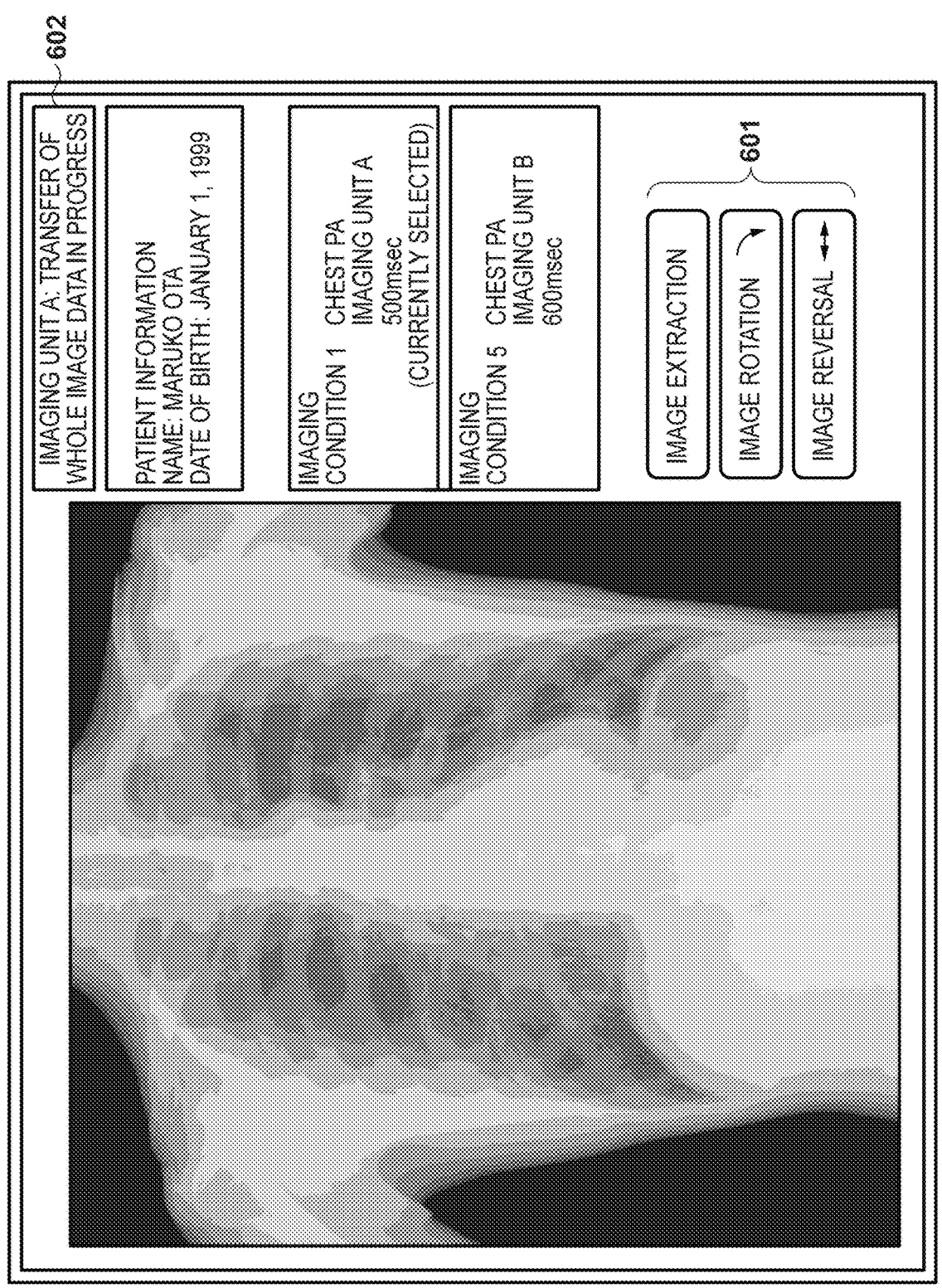
FIG. 6 is a view showing a display example on the external display device according to the embodiment.

That is, in step S106, the display control unit 1023 displays the received reduced image data on the display device 30. Furthermore, in step S107, the display control unit 1023 enables image editing of the reduced image data displayed on the display device 30. FIG. 6 is a view showing a display example of the reduced image data on the display device 30. The display control unit 1023 displays, for example, the reduced image data on the display device 30, as shown in FIG. 6, and performs display control to enable an image editing operation such as image extraction, image rotation, or image reversal. The display control unit 1023 displays an image editing portion 601 for performing the image editing operation on the display screen of the display device 30, and enables the image editing operation of the reduced image data based on an editing operation via the image editing portion 601.

In the state (FIG. 6) in which the reduced image data is displayed, the transfer processing of the reduced image data is complete in imaging unit A, and imaging unit A currently transfers the whole image data. The display control unit 1023 displays "transfer of whole image data in progress" on state display 602 of imaging unit A.

In step S108, the reception control unit 1022 determines whether the reception of the whole image data is complete. If the reception of the whole image data is complete (YES in step S108), the process advances to step S110; otherwise (NO in step S108), the process advances to step S109.

In step S109, the reception control unit 1022 determines whether the radiation imaging unit 101 has interrupted the image transfer. When the radiation imaging unit 101 interrupts the image transfer, it notifies the console 102 of the interrupt of the image transfer. Based on the notification transmitted from the radiation imaging unit 101, the reception control unit 1022 can determine whether the radiation imaging unit 101 has interrupted the image transfer. If the radiation imaging unit 101 has interrupted the image transfer (YES in step S109), the process advances to step S112; otherwise (NO in step S109), the process returns to step S108, and the same processing is executed in step S108. If it is determined in step S108 that the reception of the whole image data is complete (YES in step S108), the process advances to step S110. The reception control unit 1022 determines whether the reception of the generated radiation image data (whole image data) is complete. If the reception of the generated radiation image data (whole image data) is complete, the display control unit 1023 displays the radiation image data (whole image data) on the display device 30. The display control unit 1023 displays an image editing portion 801 for performing an image editing operation on the display screen of the display device 30, and enables the image editing operation of the whole image data based on an editing operation via the image editing portion 801.

Figure 8:
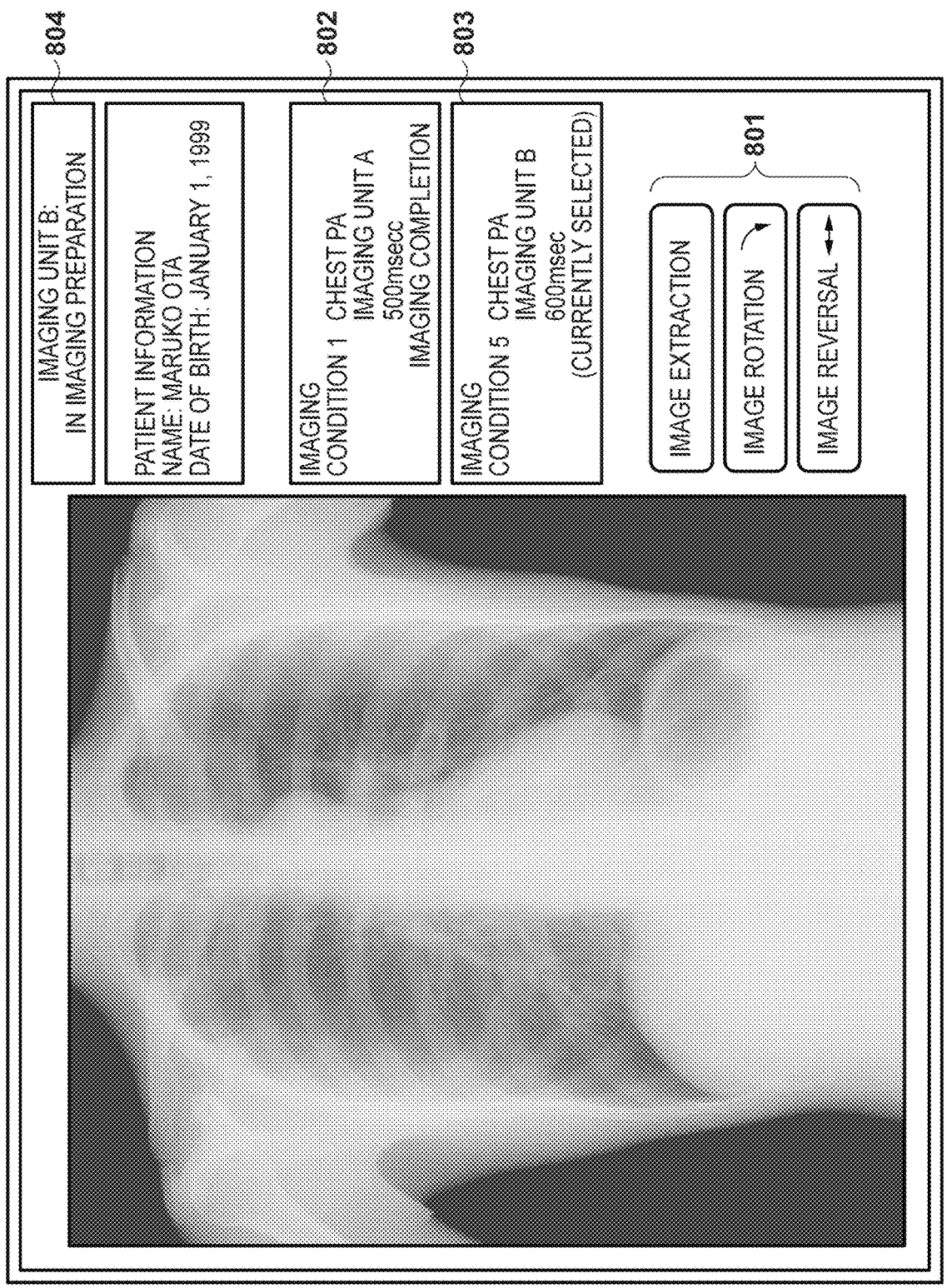
FIG. 8 is a view showing a display example on the external display device according to the embodiment.

That is, in step S110, the display control unit 1023 displays the received whole image data on the display device 30. In step S111, the reception control unit 1022 ends the reception processing of the image data. If the transfer of the image data has been interrupted, when an image transfer end instruction is input, the imaging control unit 1021 ends the interrupted image transfer in step S111. FIG. 8 is a view showing a display example of the whole image data on the display device 30. For example, the display control unit 1023 displays the whole image data on the display device 30, as shown in FIG. 8, and performs display control to enable an image editing operation such as image extraction, image rotation, or image reversal. The display control unit 1023 displays the image editing portion 801 for performing the image editing operation on the display screen of the display device 30, and enables the image editing operation of the whole image data based on an editing operation via the image editing portion 801.

In the state (FIG. 8) in which the whole image data is displayed, the transfer processing of the whole image data is complete in imaging unit A. In the display example of FIG. 8, imaging condition 1 under which imaging unit A is used is displayed in an imaging completion state (802). In next imaging, imaging condition 5 under which imaging unit B is used is displayed in a selected state (currently selected) (803). FIG. 8 shows a state in which "in imaging preparation" is currently displayed on state display 804 of the imaging unit (in this case, imaging unit B) to be used for imaging under imaging condition 5.

Since the reception control unit 1022 has determined the interrupt of the image transfer in step S105 or S109, it interrupts the reception processing of the image data in step S112.

In step S113, based on the image size captured by the radiation imaging unit 101 and the image data for which the image transfer is complete, the reception control unit 1022 calculates the progress of the image transfer indicating the percentage of completion of the transfer. That is, the reception control unit 1022 calculates the progress (transfer progress) of the image transfer indicating the percentage of the whole image data which has been received before the interrupt of the image transfer. For example, as shown in FIG. 9B, the image size captured by imaging unit A is 2800 (pixels)×3408 (pixels), and the reception control unit 1022 can calculate the progress (transfer progress) of the image transfer by obtaining the percentage of the image data, for which the image transfer is complete, with respect to the image size. In this example, imaging unit A has been exemplified. However, the same applies to a case in which another imaging unit shown in FIG. 9B is used.

Figure 7:
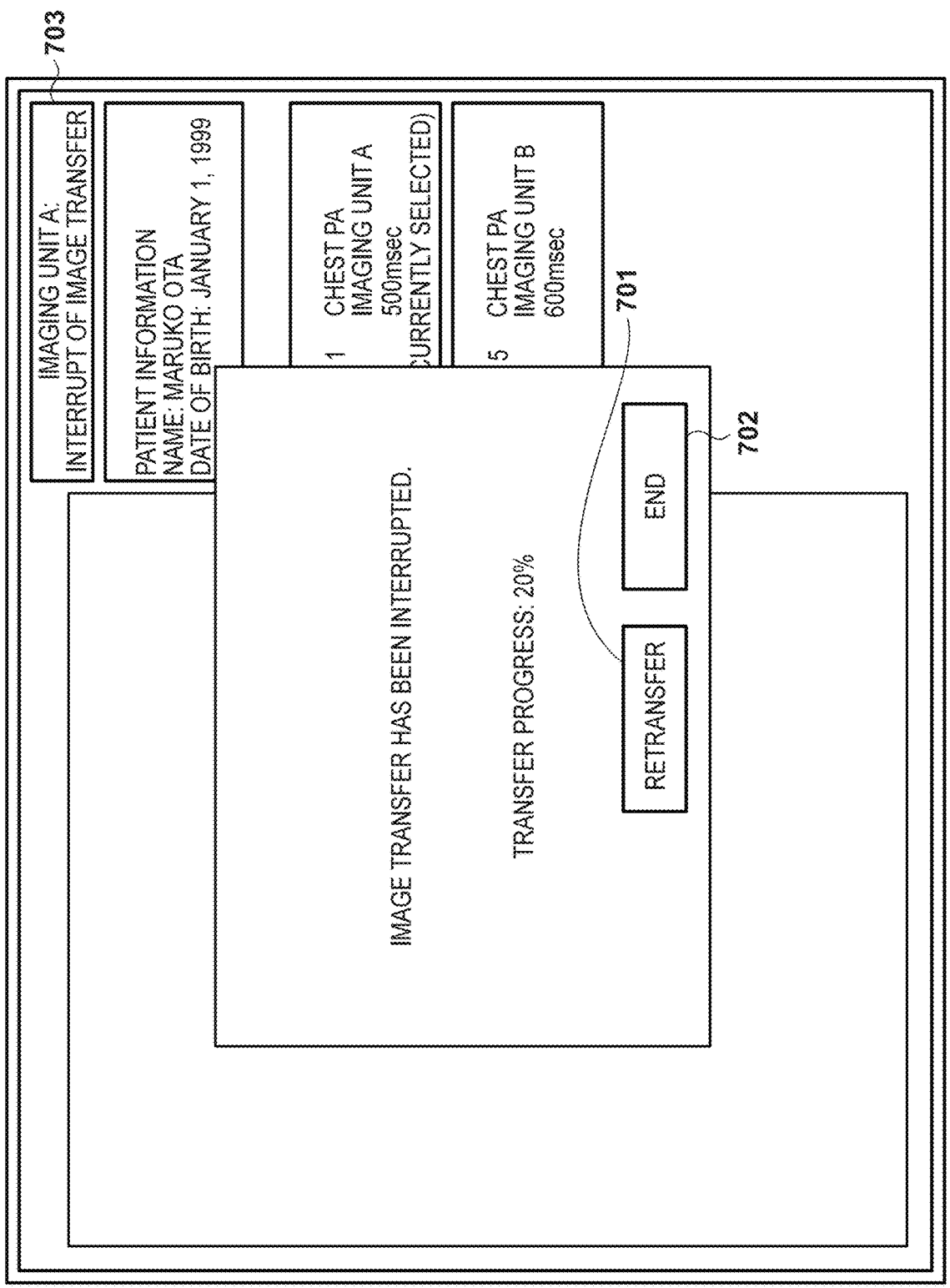
FIG. 7 is a view showing a display example of transfer progress and a transfer interrupt message on the external display device.

Furthermore, in step S114, the display control unit 1023 displays, on the display device 30, the progress (transfer progress) of the image transfer calculated in step S113 and a message for notifying the user of the interrupt of the transfer. If the transfer is interrupted, the control unit 103 of the radiation imaging unit 101 outputs a notification indicating the interrupt of the image transfer, and the display control unit 1023 displays the notification on the display device 30. The display control unit 1023 displays the progress of the image transfer on the display device 30. FIG. 7 is a view showing a display example of the progress (transfer progress) of the image transfer and the message for notifying the user of the interrupt of the transfer on the display device 30. In the state (FIG. 7) in which the transfer of the image data is interrupted, "interrupt of image transfer" is currently displayed on state display 703 of the imaging unit (in this case, imaging unit A) used for imaging. The display control unit 1023 displays, on the display screen of the display device 30, a retransfer instruction portion for instructing to retransfer the image for which the image transfer has been interrupted and an end instruction portion for instructing to end the image transfer. For example, as shown in FIG. 7, the display control unit 1023 displays, on the display screen of the display device 30, a retransfer instruction portion 701 for instructing the imaging unit to retransfer the image and an end instruction portion 702 for instructing to end the image transfer, thereby making it possible to select, based on an operation via the retransfer instruction portion 701 or the end instruction portion 702, whether to execute retransfer of the image or end the image transfer. If retransfer of the image is instructed via the retransfer instruction portion 701, the control unit 103 of the radiation imaging unit 101 performs transfer control to restart the interrupted transfer.

The operation detection unit 1024 receives information input by the operator via the retransfer instruction portion 701 or the end instruction portion 702, and inputs it to the imaging control unit 1021. Based on the information input from the operation detection unit 1024, the imaging control unit 1021 controls the radiation imaging unit. If a retransfer instruction is input, the imaging control unit 1021 requests the radiation imaging unit 101 to retransfer the interrupted image data, thereby causing the radiation imaging unit to execute retransfer of the interrupted image data. If an image transfer end instruction is input, the imaging control unit 1021 ends the interrupted image transfer.

In step S115, based on the information input from the operation detection unit 1024, the imaging control unit 1021 determines whether to retransfer the interrupted image data. If an image transfer end instruction is input (the operator presses the button of the end instruction portion 702 in FIG. 7), that is, no retransfer is performed (NO in step S115), the process advances to step S111. In step S111, the imaging control unit 1021 ends the interrupted image transfer.

On the other hand, if it is determined in step S115 that a retransfer instruction is input (the operator presses the button of the retransfer instruction portion 701 in FIG. 7), that is, retransfer is performed (YES in step S115), the process advances to step S116.

In step S116, the imaging control unit 1021 requests the radiation imaging unit 101 to retransfer the interrupted image data, thereby causing the radiation imaging unit to retransfer the interrupted image data. The process then returns to step S103. In step S103, the reception control unit 1022 starts to receive the image data retransferred from the radiation imaging unit 101. The above processing is the processing procedure of the console 102.

(Processing Procedure of Radiation Imaging Unit 101)

Figure 3:
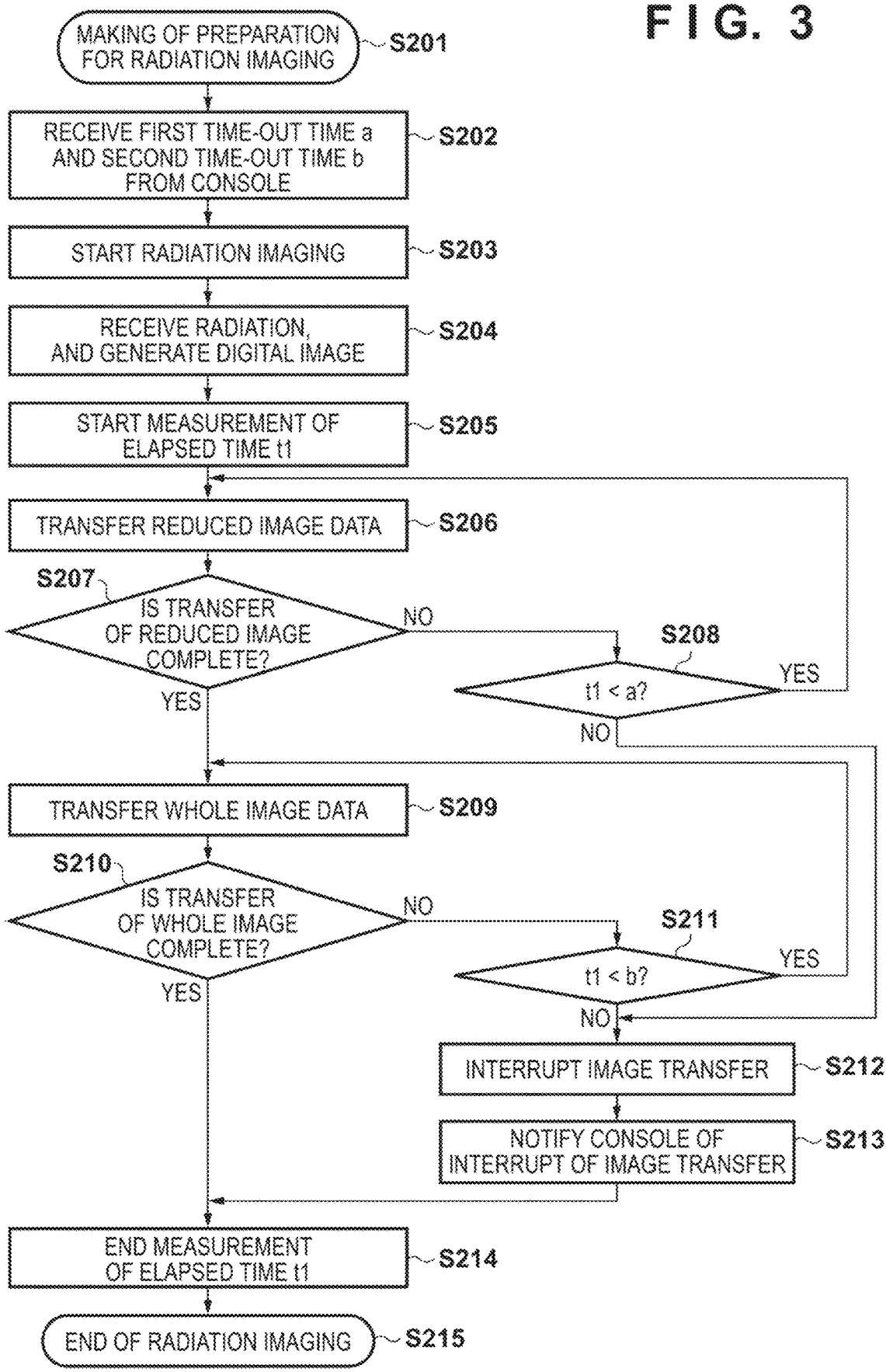
FIG. 3 is a flowchart illustrating the processing procedure of a radiation imaging unit according to the embodiment.

The processing procedure of the radiation imaging unit 101 of the radiation imaging system 10 will be described next. FIG. 3 is a flowchart illustrating a processing procedure in which the radiation imaging unit 101 of the radiation imaging system 10 executes radiation imaging, transfers image data, interrupts the transfer processing, and ends the radiation imaging.

In step S201, upon receiving, from the console 102, a notification that the radiation imaging unit 101 is to be used for imaging, the radiation imaging unit 101 prepares for radiation imaging.

In step S202, the radiation imaging unit 101 receives the first interrupt determination time (first time-out time $\underline{a}$) and second interrupt determination time (second time-out time b) transmitted from the console 102.

Next, when preparation for radiation imaging is made, the radiation imaging unit 101 starts radiation imaging in step S203. The radiation imaging unit 101 may perform radiation imaging with the radiation generation apparatus 20 using a synchronization signal, or may start radiation imaging by using, as a trigger, detection of radiation from the radiation generation apparatus 20.

Upon start of radiation imaging, in step S204 the radiation imaging unit 101 receives radiation and generates a digital image. Since the radiation imaging unit 101 transmits the generated digital image to the console 102, it starts, in step S205, measurement of an elapsed time t1 taken to perform image transfer. The radiation imaging unit 101 includes a measurement unit for measuring an elapsed time taken to transfer a radiation image, and the measurement unit measures an elapsed time after the start of transfer of a radiation image. In this embodiment, after completion of transfer of reduced image data obtained by reducing the generated radiation image, the radiation imaging unit 101 transfers the generated radiation image (whole image data).

In step S206, the radiation imaging unit 101 transfers the reduced image data. In step S207, the radiation imaging unit 101 determines whether the transfer of the reduced image data is complete. If the transfer of the radiation image is not complete, the control unit 103 of the radiation imaging unit 101 determines, based on comparison between the measured time and the set interrupt determination time, whether to continue or interrupt the transfer. If it is determined in step S207 that the transfer of the reduced image data is not complete (NO in step S207), the process advances to step S208.

In step S208, the control unit 103 of the radiation imaging unit 101 determines whether the measured time (elapsed time t1) exceeds the first time-out time a (interrupt determination time). If the elapsed time t1 exceeds the first time-out time a (interrupt determination time) (NO in step S208), the process advances to step S212. That is, if the measured time (elapsed time t1) exceeds the set time (first time-out time a (interrupt determination time)), the control unit 103 of the radiation imaging unit 101 determines to interrupt the transfer.

On the other hand, if it is determined in step S208 that the elapsed time t1 does not exceed the first time-out time a (YES in step S208), the process returns to step S206. In step S206, the radiation imaging unit 101 executes the transfer processing of the reduced image data. That is, if the measured time (elapsed time t1) does not exceed the set time (first time-out time a (interrupt determination time)), the control unit 103 of the radiation imaging unit 101 determines to continue the transfer.

If it is determined in step S207 that the transfer of the reduced image data is complete (YES in step S207), the process advances to step S209.

In step S209, the radiation imaging unit 101 transfers the whole image data obtained by imaging. In step S210, the radiation imaging unit 101 determines whether the transfer of the whole image data is complete. If the transfer of the radiation image is not complete, the control unit 103 of the radiation imaging unit 101 determines, based on comparison between the measured time and the set interrupt determination time, whether to continue or interrupt the transfer. If it is determined in step S210 that the transfer of the whole image data is not complete (NO in step S210), the process advances to step S211.

In step S211, the radiation imaging unit 101 determines whether the measured time (elapsed time t1) exceeds the second time-out time b (interrupt determination time). If the elapsed time t1 exceeds the second time-out time b (interrupt determination time) (NO in step S211), the process advances to step S212. That is, if the measured time (elapsed time t1) exceeds the set time (second time-out time b (interrupt determination time)), the control unit 103 of the radiation imaging unit 101 determines to interrupt the transfer.

On the other hand, if it is determined in step S211 that the elapsed time t1 does not exceed the second time-out time b (YES in step S211), the process returns to step S209. In step S209, the radiation imaging unit 101 executes the transfer processing of the whole image data. That is, if the measured time (elapsed time t1) does not exceed the set time (second time-out time b (interrupt determination time), the control unit 103 of the radiation imaging unit 101 determines to continue the transfer.

If it is determined in step S210 that the transfer of the whole image data is complete (YES in step S210), the process advances to step S214.

On the other hand, in step S212, since the elapsed time t1 exceeds the first time-out time a or the second time-out time b, the radiation imaging unit 101 interrupts the image transfer. In step S213, the radiation imaging unit 101 notifies the console 102 that it has interrupted the image transfer. That is, when the transfer is interrupted, the control unit 103 of the radiation imaging unit 101 outputs a notification indicating the interrupt of the image transfer. In the above-described processing procedure (step S105 or S109) of the console 102, the reception control unit 1022 can determine, based on the notification transmitted from the radiation imaging unit 101, whether the radiation imaging unit 101 has interrupted the image transfer.

In step S214, the radiation imaging unit 101 ends the measurement of the elapsed time t1. In step S215, the radiation imaging unit 101 ends the radiation imaging. The above-described processing is a processing procedure in which the radiation imaging unit 101 executes radiation imaging, transfers image data, interrupts the transfer processing, and ends the radiation imaging.

The retransfer processing procedure of the interrupted image data, which is executed by the radiation imaging unit 101, will be described next.

Figure 4:
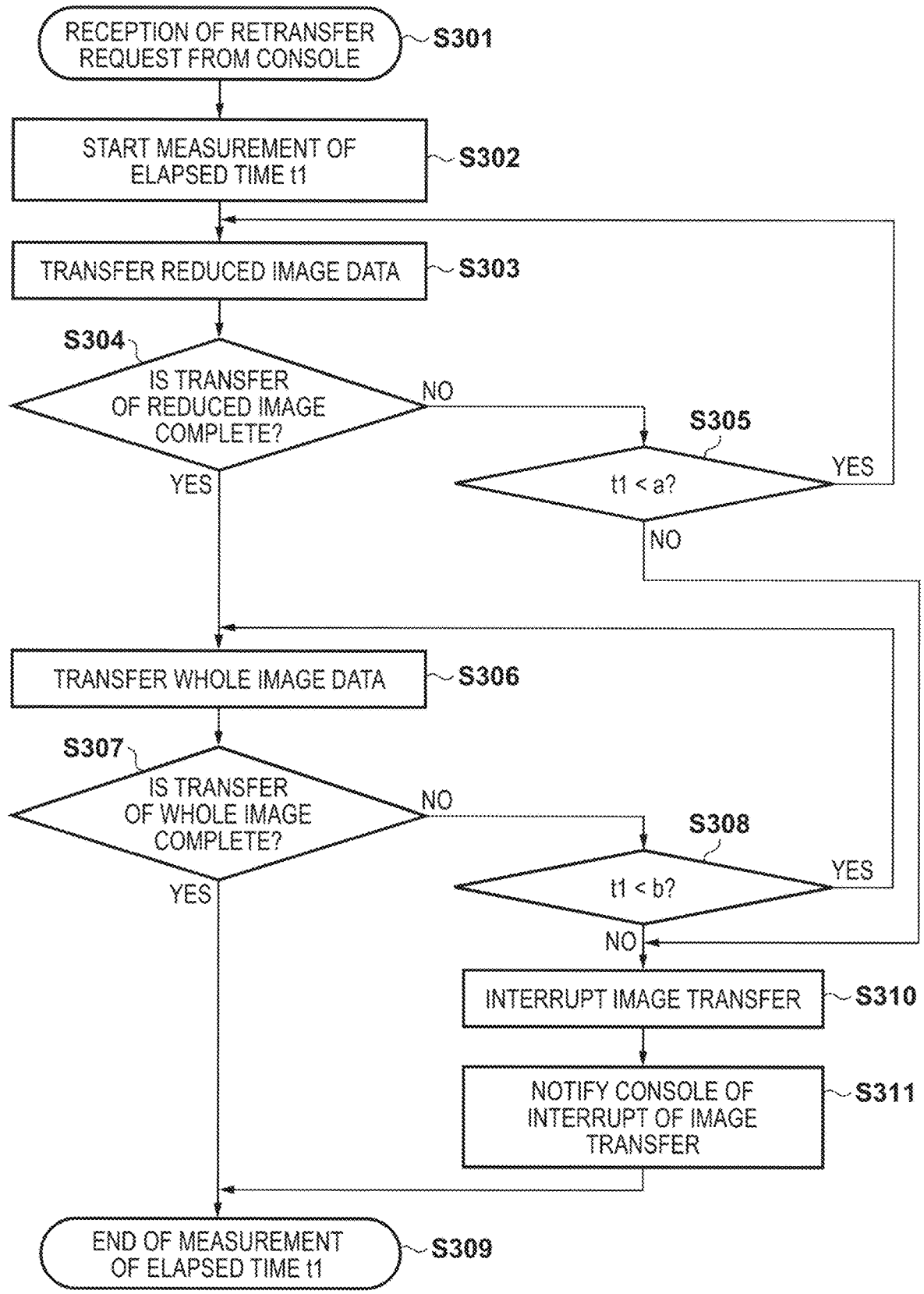
FIG. 4 is a flowchart illustrating the processing procedure of the radiation imaging unit according to the embodiment.

FIG. 4 is a flowchart illustrating the retransfer processing procedure of the image data, which is executed by the radiation imaging unit 101 in the radiation imaging system 10.

In step S301, the radiation imaging unit 101 receives a retransfer request of the image data from the console 102. The retransfer request transmitted from the console 102 corresponds to the retransfer request of the interrupted image data, which is transmitted from the imaging control unit 1021 of the console 102 in step S116 of FIG. 2. Upon receiving the retransfer request, the radiation imaging unit 101 starts image transfer, and thus starts, in step S302, measurement of the elapsed time t1 taken for the image transfer.

In step S303, the radiation imaging unit 101 transmits the reduced image data. In step S304, the radiation imaging unit 101 determines whether the transfer of the reduced image data is complete. If it is determined in step S304 that the transfer of the reduced image data is not complete (NO in step S304), the process advances to step S305.

In step S305, the radiation imaging unit 101 determines whether the elapsed time t1 exceeds the first time-out time a. If the elapsed time t1 exceeds the first time-out time a (NO in step S305), the process advances to step S310; otherwise (YES in step S305), the process returns to step S303. In step S303, the radiation imaging unit 101 executes the transfer processing of the reduced image data.

On the other hand, if it is determined in step S304 that the transfer of the reduced image data is complete (YES in step S304), the process advances to step S306.

In step S306, the radiation imaging unit 101 transfers the whole image data obtained by imaging.

In step S307, the radiation imaging unit 101 determines whether the transfer of the whole image data is complete. If it is determined in step S307 that the transfer of the whole image data is not complete (NO in step S307), the process advances to step S308.

In step S308, the radiation imaging unit 101 determines whether the elapsed time t1 exceeds the second time-out time b. If the elapsed time t1 exceeds the second time-out time b (NO in step S308), the process advances to step S310; otherwise (YES in step S308), the process returns to step S306. In step S306, the radiation imaging unit 101 executes the transfer processing of the whole image data.

On the other hand, if it is determined in step S307 that the transfer of the whole image data is complete (YES in step S307), the process advances to step S309.

In step S310, since the elapsed time t1 exceeds the first time-out time a or the second time-out time b, the radiation imaging unit 101 interrupts the image transfer. In step S311, the radiation imaging unit 101 notifies the console 102 that it has interrupted the image transfer (retransfer). In the above-described processing procedure (step S105 or S109) of the console 102, the reception control unit 1022 can determine, based on the notification transmitted from the radiation imaging unit 101, whether the radiation imaging unit 101 has interrupted the image transfer (retransfer).

In step S309, the radiation imaging unit 101 ends the measurement of the elapsed time t1, and ends the processing related to the retransfer of the interrupted image data. Note that upon receiving a retransfer request of the interrupted image data again from the console 102 (step S301), the radiation imaging unit 101 executes the processing procedure in steps S301 to S311 described with reference to FIG. 4. As described above, the time-out time (first time-out time a) from the start of the image transfer to display of the reduced image data is set short, and the time-out time (second time-out time b) from the start of the image transfer to display of the whole image data is set long. It is thus possible to implement the radiation imaging system 10 in which even if a communication path (communication environment) for image transfer is unstable, by setting the first time-out time a and the second time-out time b, it is possible to complete processing up to transfer of the reduced image data early, and transfer the whole image data slowly but reliably after completion of the transfer of the reduced image data.

If retransfer of the image is instructed via the retransfer instruction portion 701, the control unit 103 of the radiation imaging unit 101 can perform, based on pixel information indicating an interrupted pixel in the image data, transfer control to transfer the untransferred image data from the interrupted pixel. For example, if the image transfer by the radiation imaging unit 101 is interrupted, the image received by the console 102 is stored in the storage unit of the console 102, and the control unit 103 of the radiation imaging unit 101 stores pixel information indicating an interrupted pixel in the image data. Based on the pixel information indicating the interrupted pixel in the image data, the control unit 103 of the radiation imaging unit 101 may retransfer the image from the middle of the image data at which the transfer has been interrupted. Alternatively, if retransfer of the image is instructed via the retransfer instruction portion 701, the control unit 103 of the radiation imaging unit 101 can perform transfer control to transfer the image data at the start of the transfer from the beginning. For example, without storing the image received by the console 102, the control unit 103 of the radiation imaging unit 101 may transfer the image data from the beginning in retransfer of the image of the radiation imaging unit 101 without storing the pixel information indicating the interrupted pixel in the image data.

Second Embodiment

The arrangement of a radiation imaging system according to the second embodiment will be described next. In the radiation imaging system according to this embodiment, an arrangement will be explained in which a first interrupt determination time (a+α) and a second interrupt determination time (b+β) respectively different from the first interrupt determination time (first time-out time a) and second interrupt determination time (second time-out time b) both of which are set in a radiation imaging unit 101 are set in a console 102 and whether to continue or end reception of image data is determined based on the transfer status of radiation image data. The arrangement of the radiation imaging system according to the second embodiment is common to the arrangement (FIG. 1) of the radiation imaging system described in the first embodiment.

Figure 10:
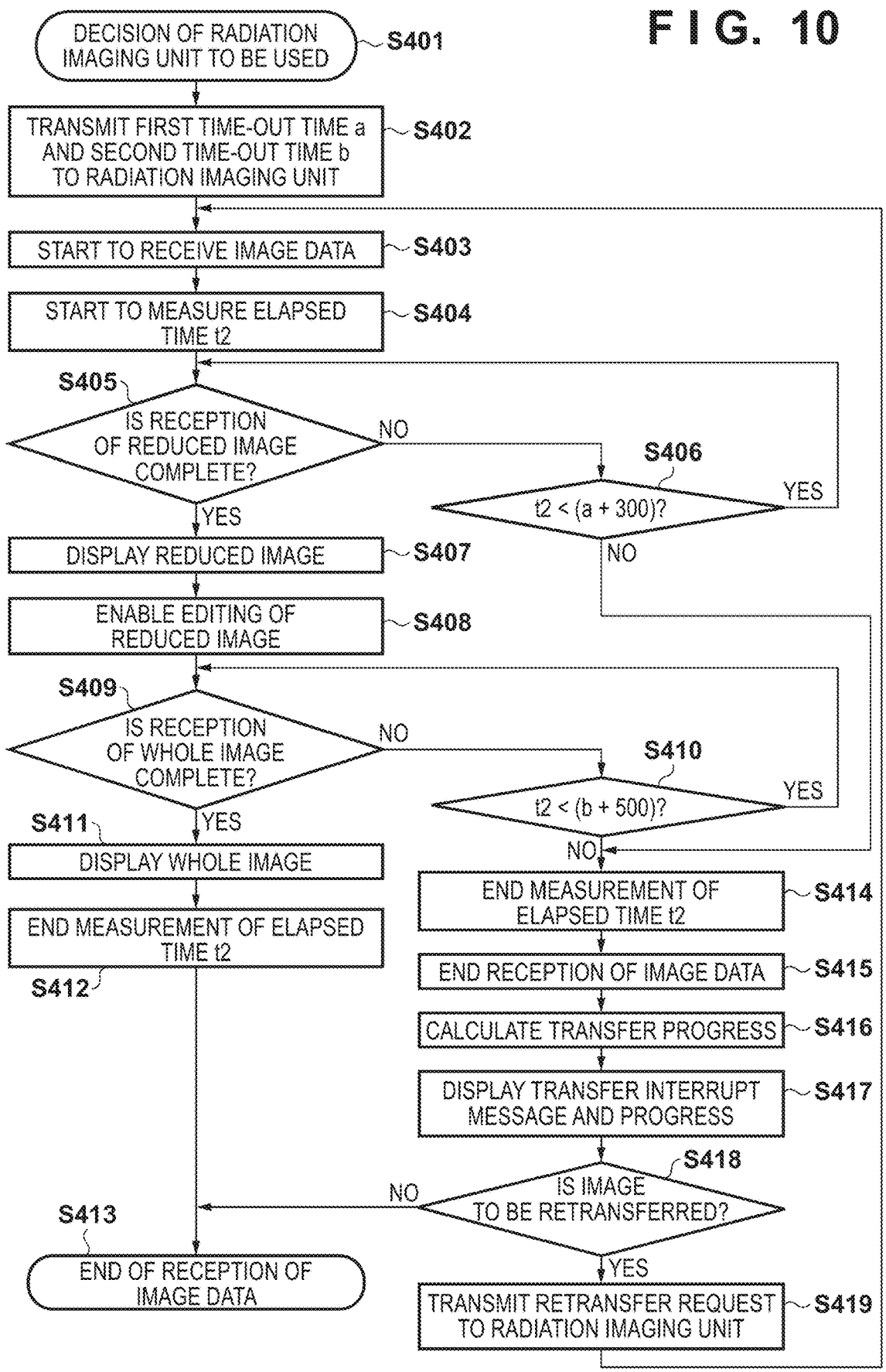
FIG. 10 is a flowchart illustrating the processing procedure of a console according to the second embodiment.

FIG. 10 is a flowchart illustrating the processing procedure of the console 102 in a radiation imaging system 10 according to the second embodiment from when the radiation imaging unit 101 to be used by the console 102 for imaging is specified to perform radiation imaging until the radiation imaging ends.

In step S401, an imaging control unit 1021 of the console 102 decides the radiation imaging unit 101 to be used for imaging among a plurality of radiation imaging units (to be also simply referred to as "imaging units" hereinafter), and sends a notification to the decided radiation imaging unit 101.

In step S402, the imaging control unit 1021 transmits, to the radiation imaging unit 101, the first interrupt determination time (first time-out time a) and second interrupt determination time (second time-out time b) corresponding to the radiation imaging unit 101 decided in step S401. The imaging control unit 1021 may decide the first time-out time a and the second time-out time b from image data display times complying with the image size of the decided imaging unit. For example, as shown in FIG. 9B, the image size of imaging unit A is 2800 (pixels)×3408 (pixels), and the imaging control unit 1021 can obtain the image data display times (reduced image data display time: 8000 msec, whole image data display time 33000 msec) corresponding to this image size from the table shown in FIG. 9A, and transmit them as the first interrupt determination time (first time-out time a) and the second interrupt determination time (second time-out time b) to the radiation imaging unit 101.

In step S403, a reception control unit 1022 starts to receive image data by using, as a trigger, the start of transmission of the image data by the radiation imaging unit 101.

In step S404, the reception control unit 1022 starts measurement of an elapsed time t2 after the start of the reception of the image data. The reception control unit 1022 includes a measurement unit for measuring an elapsed time after the start of reception, and the measurement unit measures an elapsed time after the start of reception of image data.

In step S405, the reception control unit 1022 determines whether reception of reduced image data is complete. If the reception of the reduced image data is complete (YES in step S405), the process advances to step S407. The reception control unit 1022 determines whether the reception of the reduced image data is complete. If the reception of the reduced image data is complete, a display control unit 1023 displays the reduced image data on a display device 30. On the other hand, if the reception of the reduced image data is not complete (NO in step S405), the process advances to step S406.

If the reception control unit 1022 determines whether the reception of the reduced image data is complete, and then determines that the reception of the reduced image data is not complete, it determines in step S406, based on comparison between the measured time and a time (first time-out time a+α (arbitrarily settable additional time)) based on the first interrupt determination time, whether to continue or end the reception of the reduced image data. The time based on the first interrupt determination time is a time obtained by adding the settable additional time α to the first interrupt determination time a. The reception control unit 1022 determines whether the elapsed time t2 exceeds the time (first time-out time a+additional time α) based on the first interrupt determination time. The first time-out time in the console 102 may be set longer than the time-out time of the radiation imaging unit 101 by increasing the time set in the radiation imaging unit 101. In this example, the time obtained by adding the additional time (300 msec) to the first time-out time a, of which the radiation imaging unit 101 has been notified, is set as the first time-out time in the console 102.

If the elapsed time t2 exceeds the first time-out time (a+300 msec) (NO in step S406), the process advances to step S414. On the other hand, if it is determined in step S406 that the elapsed time t2 does not exceed the first time-out time (a+300 msec) (YES in step S406), the process returns to step S405, and the same processing is executed in step S405. If it is determined in step S405 that the reception of the reduced image data is complete (YES in step S405), the process advances to step S407.

In step S407, the display control unit 1023 displays the received reduced image data on the display device 30. In step S408, the display control unit 1023 enables image editing of the reduced image data displayed on the display device 30. FIG. 6 is a view showing a display example of the reduced image data on the display device 30. For example, the display control unit 1023 displays the reduced image data on the display device 30, as shown in FIG. 6, and performs display control to enable an image editing operation such as image extraction, image rotation, or image reversal. The display control unit 1023 displays an image editing portion 601 for performing the image editing operation on the display screen of the display device 30, and enables the image editing operation of the reduced image data based on an editing operation via the image editing portion 601.

In step S409, the reception control unit 1022 determines whether reception of whole image data is complete. If the reception of the whole image data is complete (YES in step S409), the process advances to step S411; otherwise (NO in step S409), the process advances to step S410.

If the reception control unit 1022 determines whether the reception of the generated radiation image data (whole image data) is complete, and determines that the reception of the generated radiation image data is not complete, it determines, in step S410, based on comparison between the measured time and the time (the second time-out time b+β (arbitrarily settable additional time)) based on the second interrupt determination time, whether to continue or end the reception of the generated radiation image data. The time based on the second interrupt determination time is a time obtained by adding the settable additional time β to the second interrupt determination time b. The reception control unit 1022 determines whether the elapsed time t2 exceeds the time (second time-out time b+additional time β) based on the second interrupt determination time. The second time-out time in the console 102 may be set longer than the time-out time of the radiation imaging unit 101 by increasing the time set in the radiation imaging unit 101. In this example, the time obtained by adding the additional time (500 msec) to the second time-out time b, of which the radiation imaging unit 101 has been notified, is set as the second time-out time in the console 102.

If the elapsed time t2 exceeds the second time-out time (b+500 msec) (NO in step S410), the process advances to step S414. On the other hand, if it is determined in step S410 that the elapsed time t2 does not exceed the second time-out time (b+500 msec) (YES in step S410), the process returns to step S409, and the same processing is executed in step S409. If it is determined in step S409 that the reception of the whole image data is complete (YES in step S409), the process advances to step S411.

In step S411, the display control unit 1023 displays the received whole image data on the display device 30. In step S412, the reception control unit 1022 ends the measurement of the elapsed time t2. In step S413, the reception control unit 1022 ends the reception processing of the image data. For example, the display control unit 1023 displays the whole image data on the display device 30, as shown in FIG. 8, and performs display control to enable an image editing operation such as image extraction, image rotation, or image reversal. The display control unit 1023 displays an image editing portion 801 for performing the image editing operation on the display screen of the display device 30, and enables the image editing operation of the whole image data based on an editing operation via the image editing portion 801.

On the other hand, in step S414, the reception control unit 1022 ends the measurement of the elapsed time t2 since it is determined in step S406 or S410 that the elapsed time exceeds the time-out time. In step S415, the reception control unit 1022 ends the reception of the image data.

In step S416, the reception control unit 1022 calculates the progress of the image transfer indicating the percentage of completion of the transfer based on the image size captured by the radiation imaging unit 101 and the image data for which the image transfer is complete. That is, the reception control unit 1022 calculates the progress (transfer progress) of the image transfer indicating the percentage of the whole image data which has been received before the interrupt of the image transfer.

Furthermore, in step S417, the display control unit 1023 displays, on the display device 30, the progress (transfer progress) of the image transfer calculated in step S416 and a message for notifying the user of the interrupt of the transfer. As shown in FIG. 7, the display control unit 1023 displays, on the display screen of the display device 30, a retransfer instruction portion 701 for instructing the imaging unit to retransfer the image and an end instruction portion 702 for instructing to end the image transfer, thereby making it possible to select, based on an operation via the retransfer instruction portion 701 or the end instruction portion 702, whether to execute retransfer of the image or end the image transfer.

An operation detection unit 1024 receives information input by the operator via the retransfer instruction portion 701 or the end instruction portion 702, and inputs it to the imaging control unit 1021. Based on the information input from the operation detection unit 1024, the imaging control unit 1021 controls the radiation imaging unit. If a retransfer instruction is input, the imaging control unit 1021 requests the radiation imaging unit 101 to retransfer the interrupted image data, thereby causing the radiation imaging unit to execute retransfer of the interrupted image data. If an image transfer end instruction is input, the imaging control unit 1021 ends the interrupted image transfer.

In step S418, based on the information input from the operation detection unit 1024, the imaging control unit 1021 determines whether to retransfer the interrupted image data. If an image transfer end instruction is input (the operator presses the button of the end instruction portion 702 in FIG. 7), that is, no retransfer is performed (NO in step S418), the process advances to step S413. In step S413, the imaging control unit 1021 ends the interrupted image transfer.

On the other hand, if it is determined in step S418 that a retransfer instruction is input (the operator presses the button of the retransfer instruction portion 701 in FIG. 7), that is, retransfer is performed (YES in step S418), the process advances to step S419.

In step S419, the imaging control unit 1021 requests the radiation imaging unit 101 to retransfer the interrupted image data, thereby causing the radiation imaging unit to retransfer the interrupted image data. The process then returns to step S403. In step S403, the reception control unit 1022 starts to receive the image data retransferred from the radiation imaging unit 101. The above processing is the processing procedure of the console 102.

As described above, it is possible to obtain the same effects as in the first embodiment with the arrangement in which a time-out of image transfer is determined in the console 102. That is, the time-out time (first time-out time) from the start of image transfer to display of reduced image data is set short, and the time-out time (second time-out time) from the start of image transfer to display of whole image data is set long. It is thus possible to implement the radiation imaging system 10 in which even if a communication path (communication environment) for image transfer is unstable, by setting the first time-out time and the second time-out time, it is possible to complete processing up to transfer of the reduced image data early, and transfer the whole image data slowly but reliably after completion of the transfer of the reduced image data.

Third Embodiment

The arrangement of a radiation imaging system according to the third embodiment will be described next. In the radiation imaging system according to this embodiment, an arrangement will be explained in which a first interrupt determination time (first time-out time a+c) and a second interrupt determination time (second time-out time b+c) are set in consideration of an accumulation time (c) of radiation in a radiation imaging unit 101, and whether image transfer has been interrupted is determined. The arrangement of the radiation imaging system according to third embodiment is common to the arrangement (FIG. 1) of the radiation imaging system described in the first embodiment.

Figure 11:
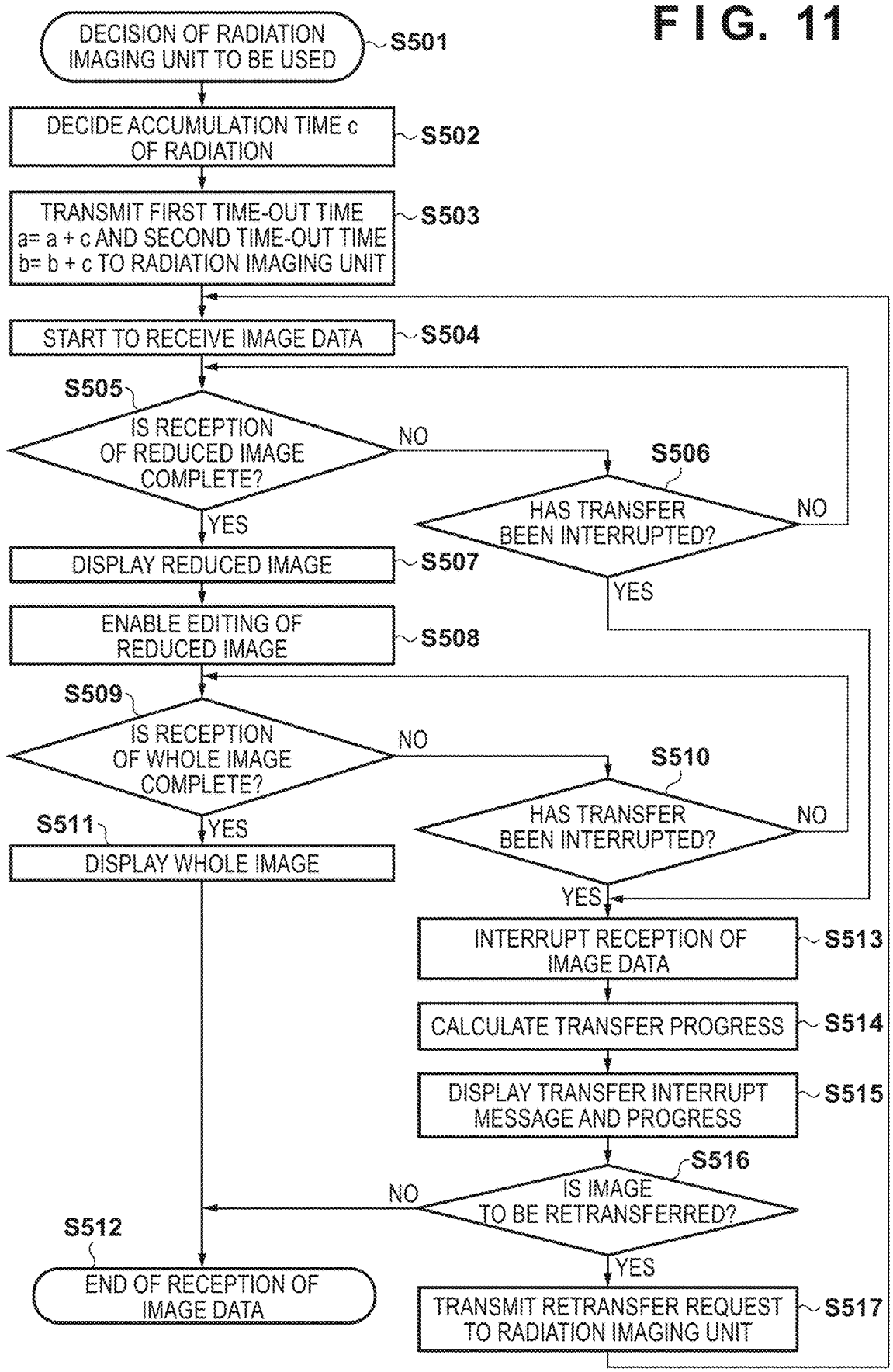
FIG. 11 is a flowchart illustrating the processing procedure of a console according to the third embodiment.

FIG. 11 is a flowchart illustrating the processing procedure of a console 102 in a radiation imaging system 10 according to the third embodiment from when the radiation imaging unit 101 to be used by the console 102 is specified to perform radiation imaging until the radiation imaging ends.

In step S501, an imaging control unit 1021 of the console 102 decides the radiation imaging unit 101 to be used for imaging among a plurality of radiation imaging units (to be also simply referred to as "imaging units" hereinafter), and sends a notification to the decided radiation imaging unit 101. FIG. 5 is a view showing a display example on a display device 30. For example, on a screen displayed on the display device 30 shown in FIG. 5, the state of the radiation imaging unit to be used for radiation imaging, patient information, and imaging conditions are displayed. A linked imaging unit is set in each imaging condition. In the display example of FIG. 5, for example, imaging unit A corresponds to imaging condition 1 (imaging part: CHESTPA, time: 500 msec), and imaging unit B corresponds to imaging condition 5 (imaging part: CHESTPA, time: 600 msec). Based on selection of the imaging condition input via a GUI, an external operation device, or the like, the console 102 can decide the radiation imaging unit 101 to be used for radiation imaging. In the display example of FIG. 5, imaging condition 1 is in a selected state (currently selected), and "in imaging preparation" is currently displayed on state display 501 of the imaging unit (in this case, imaging unit A) to be used for imaging under imaging condition 1.

In step S502, the imaging control unit 1021 decides the accumulation time c of radiation based on the imaging condition. FIG. 12 is a table showing an example of a combination of the imaging condition and the accumulation time. The imaging control unit 1021 includes a nonvolatile storage unit for storing the table shown in FIG. 12. For example, as shown in FIG. 12, an imaging unit to be used, an imaging part, an accumulation time, an imaging direction, and the like are associated with each imaging condition. The accumulation time corresponding to imaging condition 1 selected in FIG. 5 is 500 msec. Thus, the imaging control unit 1021 decides 500 msec as the accumulation time c of radiation.

In step S503, the imaging control unit 1021 transmits, to the radiation imaging unit 101, a first time-out time $\underline{a}$ (=a+c) and a second time-out time b (=b+c) corresponding to the radiation imaging unit 101 decided in step S501. The imaging control unit 1021 may decide the first time-out time $\underline{a}$ and the second time-out time b based on image data display times complying with the image size of the decided imaging unit (FIGS. 9A and 9B). Then, the imaging control unit 1021 obtains, as the first time-out time $\underline{a}$ (=a+c) and the second time-out time b (=b+c), times by adding the accumulation time c of radiation to the first time-out time $\underline{a}$ and the second time-out time b. As shown in FIG. 9B, for example, the image size of imaging unit A is 2800 (pixels)× 3408 (pixels), and the imaging control unit 1021 can obtain, from the table shown in FIG. 9A, the image data display times (reduced image data display time: 8000 msec, whole image data display time: 33000 msec) corresponding to this image size, add the accumulation time c of radiation to the obtained times, and transmit the thus obtained times as the first interrupt determination time (first time-out time a=(a+c)) and the second interrupt determination time (second time-out time b=(b+c)) to the radiation imaging unit 101. The radiation imaging unit 101 controls transfer by determining, based on the first interrupt determination time (first time-out time a=(a+c)) and the second interrupt determination time (second time-out time b=(b+c)), whether to continue or interrupt transfer. More specifically, in the flowcharts of FIGS. 3 and 4 which illustrate the processing procedure of the radiation imaging unit 101, in steps S208 and S305, the determination processing is performed based on the first interrupt determination time (first time-out time a=(a+c)). In steps S211 and S308, the determination processing is performed based on the second interrupt determination time (second time-out time b=(b+c)). That is, the first interrupt determination time and the second interrupt determination time are set based on the accumulation time c of radiation in the radiation imaging unit 101, which is decided in accordance with the imaging condition.

In step S504, a reception control unit 1022 starts to receive image data by using, as a trigger, the start of transmission of the image data by the radiation imaging unit 101.

In step S505, the reception control unit 1022 determines whether reception of reduced image data is complete. If the reception of the reduced image data is complete (YES in step S505), the process advances to step S507; otherwise (NO in step S505), the process advances to step S506.

In step S506, the reception control unit 1022 determines whether the radiation imaging unit 101 has interrupted the image transfer. If the radiation imaging unit 101 has interrupted the image transfer, it notifies the console 102 of the interrupt of the image transfer. Based on the notification transmitted from the radiation imaging unit 101, the reception control unit 1022 can determine whether the radiation imaging unit 101 has interrupted the image transfer. If the radiation imaging unit 101 has interrupted the image transfer (YES in step S506), the process advances to step S513; otherwise (NO in step S506), the process returns to step S505, and the same processing is executed in step S505. If it is determined in step S505 that the reception of the reduced image data is complete (YES in step S505), the process advances to step S507.

In step S507, a display control unit 1023 displays the received reduced image data on the display device 30. Furthermore, in step S508, the display control unit 1023 enables image editing of the reduced image data displayed on the display device 30. FIG. 6 is a view showing a display example of the reduced image data on the display device 30. The display control unit 1023 displays, for example, the reduced image data on the display device 30, as shown in FIG. 6, and performs display control to enable an image editing operation such as image extraction, image rotation, or image reversal. The display control unit 1023 displays an image editing portion 601 for performing the image editing operation on the display screen of the display device 30, and enables the image editing operation of the reduced image data based on an editing operation via the image editing portion 601.

In the state (FIG. 6) in which the reduced image data is displayed, the transfer processing of the reduced image data is complete in imaging unit A, and imaging unit A currently transfers whole image data. The display control unit 1023 displays "transfer of whole image data in progress" on state display 602 of imaging unit A.

In step S509, the reception control unit 1022 determines whether the reception of the whole image data is complete. If the reception of the whole image data is complete (YES in step S509), the process advances to step S511; otherwise (NO in step S509), the process advances to step S510.

In step S510, the reception control unit 1022 determines whether the radiation imaging unit 101 has interrupted the image transfer. If the radiation imaging unit 101 has interrupted the image transfer, it notifies the console 102 of the interrupt of the image transfer. Based on the notification transmitted from the radiation imaging unit 101, the reception control unit 1022 can determine whether the radiation imaging unit 101 has interrupted the image transfer. If the radiation imaging unit 101 has interrupted the image transfer (YES in step S510), the process advances to step S513; otherwise (NO in step S510), the process returns to step S509, and the same processing is executed in step S509. If it is determined in step S509 that the reception of the whole image data is complete (YES in step S509), the process advances to step S511.

In step S511, the display control unit 1023 displays the received whole image data on the display device 30. In step S512, the reception control unit 1022 ends the reception processing of the image data. If the transfer of the image data has been interrupted, when an image transfer end instruction is input, the imaging control unit 1021 ends the interrupted image transfer in step S512. FIG. 8 is a view showing a display example of the whole image data on the display device 30. For example, the display control unit 1023 displays the whole image data on the display device 30, as shown in FIG. 8, and performs display control to enable an image editing operation such as image extraction, image rotation, or image reversal. The display control unit 1023 displays an image editing portion 801 for performing the image editing operation on the display screen of the display device 30, and enables the image editing operation of the whole image data based on an editing operation via the image editing portion 801.

In the state (FIG. 8) in which the whole image data is displayed, the transfer processing of the whole image data is complete in imaging unit A. In the display example of FIG. 8, imaging condition 1 under which imaging unit A is used is displayed in an imaging completion state (802). In next imaging, imaging condition 5 under which imaging unit B is used is displayed in a selected state (currently selected) (803). FIG. 8 shows a state in which "in imaging preparation" is currently displayed on state display 804 of the imaging unit (in this case, imaging unit B) to be used for imaging under imaging condition 5.

Since the reception control unit 1022 has determined the interrupt of the image transfer in step S506 or S510, it interrupts the reception processing of the image data in step S513.

In step S514, based on the image size captured by the radiation imaging unit 101 and the image data for which the image transfer is complete, the reception control unit 1022 calculates the progress of the image transfer indicating the percentage of completion of the transfer. That is, the reception control unit 1022 calculates the progress (transfer progress) of the image transfer indicating the percentage of the whole image data which has been received before the interrupt of the image transfer. For example, as shown in FIG. 9B, the image size captured by imaging unit A is 2800 (pixels)×3408 (pixels), and the reception control unit 1022 can calculate the progress (transfer progress) of the image transfer by obtaining the percentage of the image data, for which the image transfer is complete, with respect to the image size. In this example, imaging unit A has been exemplified. However, the same applies to a case in which another imaging unit shown in FIG. 9B is used.

Furthermore, in step S515, the display control unit 1023 displays, on the display device 30, the progress (transfer progress) of the image transfer calculated in step S514 and a message for notifying the user of the interrupt of the transfer. FIG. 7 is a view showing a display example of the progress (transfer progress) of the image transfer and the message for notifying the user of the interrupt of the transfer on the display device 30. In the state (FIG. 7) in which the transfer of the image data is interrupted, "interrupt of image transfer" is currently displayed on state display 703 of the imaging unit (in this case, imaging unit A) used for imaging. As shown in FIG. 7, the display control unit 1023 displays, on the display screen of the display device 30, a retransfer instruction portion 701 for instructing the imaging unit to retransfer the image and an end instruction portion 702 for instructing to end the image transfer, thereby making it possible to select, based on an operation via the retransfer instruction portion 701 or the end instruction portion 702, whether to execute retransfer of the image or end the image transfer.

An operation detection unit 1024 receives information input by the operator via the retransfer instruction portion 701 or the end instruction portion 702, and inputs it to the imaging control unit 1021. Based on the information input from the operation detection unit 1024, the imaging control unit 1021 controls the radiation imaging unit. If a retransfer instruction is input, the imaging control unit 1021 requests the radiation imaging unit 101 to retransfer the interrupted image data, thereby causing the radiation imaging unit to execute retransfer of the interrupted image data. If an image transfer end instruction is input, the imaging control unit 1021 ends the interrupted image transfer.

In step S516, based on the information input from the operation detection unit 1024, the imaging control unit 1021 determines whether to retransfer the interrupted image data.

If an image transfer end instruction is input (the operator presses the button of the end instruction portion 702 in FIG. 7), that is, no retransfer is performed (NO in step S516), the process advances to step S512. In step S512, the imaging control unit 1021 ends the interrupted image transfer.

On the other hand, if it is determined in step S516 that a retransfer instruction is input (the operator presses the button of the retransfer instruction portion 701 in FIG. 7), that is, retransfer is performed (YES in step S516), the process advances to step S517.

In step S517, the imaging control unit 1021 requests the radiation imaging unit 101 to retransfer the interrupted image data, thereby causing the radiation imaging unit to retransfer the interrupted image data. The process then returns to step S504. In step S504, the reception control unit 1022 starts to receive the image data retransferred from the radiation imaging unit 101. The above processing is the processing procedure of the console 102.

As described above, it is possible to adjust the time-out times to more appropriate numerical values by adding, based on the imaging condition, a processing time such as the accumulation time of radiation which influences the image transfer time, and changing the first and second time-out times based on the imaging condition.

By adding the accumulation time of radiation, the time-out time (first time-out time (a+c)) from the start of the image transfer to display of the reduced image data is set short, and the time-out time (second time-out time (b+c)) from the start of the image transfer to display of the whole image data is set long. It is thus possible to implement the radiation imaging system 10 in which even if a communication path (communication environment) for image transfer is unstable, by setting the first time-out time (a+c) and the second time-out time (b+c), it is possible to complete processing up to transfer of the reduced image data early, and transfer the whole image data slowly but reliably after completion of the transfer of the reduced image data.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a continuation of U.S. application Ser. No. 15/475,386, filed on Mar. 31, 2017, which claims the benefit of Japanese Patent Application No. 2016-078431, filed Apr. 8, 2016, which is hereby incorporated by reference herein in its entirety.

What is claimed is:

1. A radiation imaging system, comprising:
a console; and
an imaging unit; and;
said imaging unit being configured to transfer to said console a radiation image, said radiation image having been generated based on received radiation;
said console being configured to set a first interrupt determination time for determining an interrupt of transfer of reduced image data of the radiation image; and
said radiation imaging system being configured to interrupt the transfer of the reduced image data when an elapsed time taken to transfer the reduced image exceeds the first interrupt determination time, wherein whole image data of the radiation image data is transferred when the transfer of the reduced image data is complete within an elapse of the first interrupt determination time.

2. The system according to claim 1, wherein the console is configured to set a second interrupt determination time for determining an interrupt of transfer of whole image data of the radiation image data.

3. The system according to claim 1, wherein after completion of transfer of reduced image data obtained by reducing image size of the generated radiation image, the imaging unit transfers the generated radiation image.

4. The system according to claim 2, wherein the radiation imaging system includes a measurement unit configured to measure an elapsed time taken to transfer the radiation image,
the radiation imaging system determines whether to continue or interrupt to transfer the reduced image data based on comparison between the measured time and the first interrupt determination time if the transfer of the reduced image data is not complete, and
the radiation imaging system determines whether to continue or interrupt to transfer the whole image data based on comparison between the measured time and the second interrupt determination time if the transfer of the whole image data is not complete.

5. The system according to claim 2, wherein the radiation imaging system determines to continue to transfer the reduced image data if the measured time does not exceed the first interrupt determination time, and
the radiation imaging system determines to continue to transfer the whole image data if the measured time does not exceed the second interrupt determination time.

6. The system according to claim 4, wherein if the transfer is interrupted, the radiation imaging system outputs a notification indicating an interrupt of image transfer.

7. The system according to claim 6, further comprising a display control unit configured to display the notification on a display unit.

8. The system according to claim 7, wherein the display control unit displays on a display screen of the display unit a retransfer instruction unit configured to instruct to retransfer image data for which the image transfer has been interrupted and an end instruction unit configured to instruct to end the image transfer.

9. The system according to claim 8, wherein the radiation imaging system performs transfer control to restart the interrupted transfer when retransfer of the image data is instructed from the retransfer instruction unit.

10. The system according to claim 9, wherein the radiation imaging system performs transfer control to transfer untransferred image data from the interrupted pixel based on pixel information indicating an interrupted pixel in image data when retransfer of the image data is instructed from the retransfer instruction unit.

11. The system according to claim 9, wherein the radiation imaging system performs transfer control to transfer image data at the start of transfer from the beginning when retransfer of the image is instructed from the retransfer instruction unit.

12. The system according to claim 2, wherein the second interrupt determination time is a time longer than the first interrupt determination time.

13. The system according to claim 8, wherein the first interrupt determination time is a time taken to display the reduced image data on the display unit, and the second interrupt determination time is a time taken to display the whole image data on the display unit.

14. The system according to claim 1, further comprising a reception control unit configured to receive the transferred image, wherein
the reception control unit calculates progress of the image transfer indicating a percentage of completion of the transfer based on an image size captured by the imaging unit and image data for which image transfer is complete.

15. The system according to claim 13, wherein a time based on the first interrupt determination time is a time obtained by adding a settable additional time to the first interrupt determination time, and a time based on the second interrupt determination time is a time obtained by adding a settable additional time to the second interrupt determination time.

16. The system according to claim 2, wherein the first interrupt determination time and the second interrupt determination time are set based on an accumulation time of radiation in the imaging unit, which is decided based on an imaging condition.

17. A radiation imaging method comprising:
transferring a radiation image generated based on received radiation to a console;
setting a first interrupt determination time for determining an interrupt of transfer of reduced image data of the radiation image;
interrupting the transfer of the reduced image data in a case where an elapsed time taken to transfer the reduced image exceeds the first interrupt determination time; and
transferring whole image data of the radiation image data in a case where the transfer of the reduced image data is complete within an elapse of the first interrupt determination time.

18. A computer-readable storage medium storing a program that causes a computer to execute each step of a radiation imaging method, the method comprising:
transferring a radiation image generated based on received radiation to a console;
setting a first interrupt determination time for determining an interrupt of transfer of reduced image data of the radiation image;
interrupting the transfer of the reduced image data in a case where an elapsed time taken to transfer the reduced image exceeds the first interrupt determination time; and
transferring whole image data of the radiation image data in a case where the transfer of the reduced image data is complete within an elapse of the first interrupt determination time.

* * * * *